United States Patent
Iwamasa

(10) Patent No.: US 9,526,579 B2
(45) Date of Patent: Dec. 27, 2016

(54) COMBINATION DIFFUSED AND FOCUSED FIBER OPTIC FOR DIAGNOSIS AND TREATMENT OF DISEASED CELLS

(71) Applicant: Boston Scientific Scimed, Inc., Maple Grove, MN (US)

(72) Inventor: Lauretta A. Iwamasa, San Francisco, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 168 days.

(21) Appl. No.: 14/200,868

(22) Filed: Mar. 7, 2014

(65) Prior Publication Data
US 2014/0276691 A1    Sep. 18, 2014

Related U.S. Application Data

(60) Provisional application No. 61/777,187, filed on Mar. 12, 2013.

(51) Int. Cl.
| | |
|---|---|
| *A61B 18/22* | (2006.01) |
| *A61B 5/00* | (2006.01) |
| *G02B 6/26* | (2006.01) |
| *A61B 5/20* | (2006.01) |

(52) U.S. Cl.
CPC ............ *A61B 18/22* (2013.01); *A61B 5/0071* (2013.01); *A61B 5/0084* (2013.01); *G02B 6/262* (2013.01); *A61B 5/202* (2013.01); *A61B 2562/0233* (2013.01)

(58) Field of Classification Search
CPC ..... A61B 18/22; A61B 5/0071; A61B 5/0084; A61B 2562/0233; A61B 5/202; G02B 6/262

USPC .......................................................... 606/12
See application file for complete search history.

(56) References Cited

U.S. PATENT DOCUMENTS

| | | | | |
|---|---|---|---|---|
| 5,337,381 | A * | 8/1994 | Biswas | A61N 5/0601 385/128 |
| 6,174,291 | B1 * | 1/2001 | McMahon | A61B 5/0071 600/564 |
| 2001/0055462 | A1 * | 12/2001 | Seibel | A61B 1/00048 385/147 |
| 2005/0031541 | A1 * | 2/2005 | Gierskcky | A61K 41/0061 424/9.6 |

(Continued)

OTHER PUBLICATIONS

Zaak, et al., "Routine Use of Photodynamic Diagnosis of Bladder Cancer: Practical and Economic Issues," European Urology Supplements 7 (2008) 536-541 (6 pages).

(Continued)

*Primary Examiner* — Gary Jackson
*Assistant Examiner* — Joshua Rosefelt
(74) *Attorney, Agent, or Firm* — Bookoff McAndrews, PLLC

(57) ABSTRACT

A method of treating diseased cells including the steps of instilling an optical imaging agent to a tissue of a patient, accessing the tissue with a device comprising a fiber tip, emitting a first light from the fiber tip and photodynamically diagnosing abnormal cells, and emitting a second light from the fiber tip to treat the abnormal cells. The first light can be a first power blue light and the second light can be a second power blue light, where the first power blue light can be a lower power than the second power blue light.

20 Claims, 2 Drawing Sheets

(56) References Cited

U.S. PATENT DOCUMENTS

2007/0263975 A1* 11/2007 Boutoussov .......... A61B 18/22
385/146
2007/0269837 A1* 11/2007 McGreevy .......... A61B 5/0059
435/7.23

OTHER PUBLICATIONS

Jocham, et al., Photodynamic Diagnosis in Urology: State-of-the-Art, Eur Urol (2008), doi:10.1016/j.eururo.2007.11.048 (13 pages).
Jichlinski, et al., "Photodynamic Diagnosis in Non-Muscle-Invasive Bladder Cancer," European Urology Supplements 7 (2008) 529-535 (7 pages).

* cited by examiner

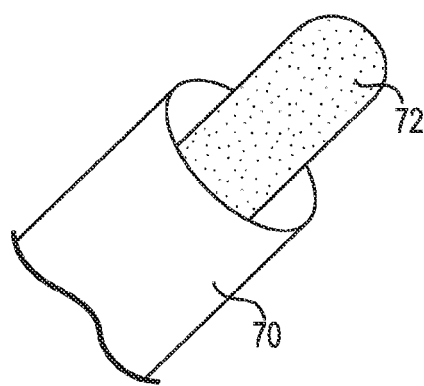
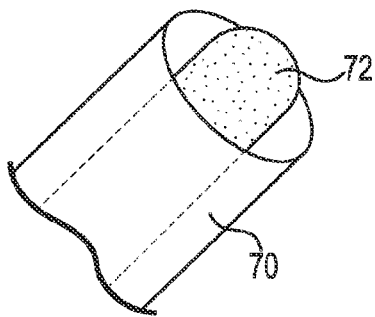
Fig. 7a    Fig. 7b
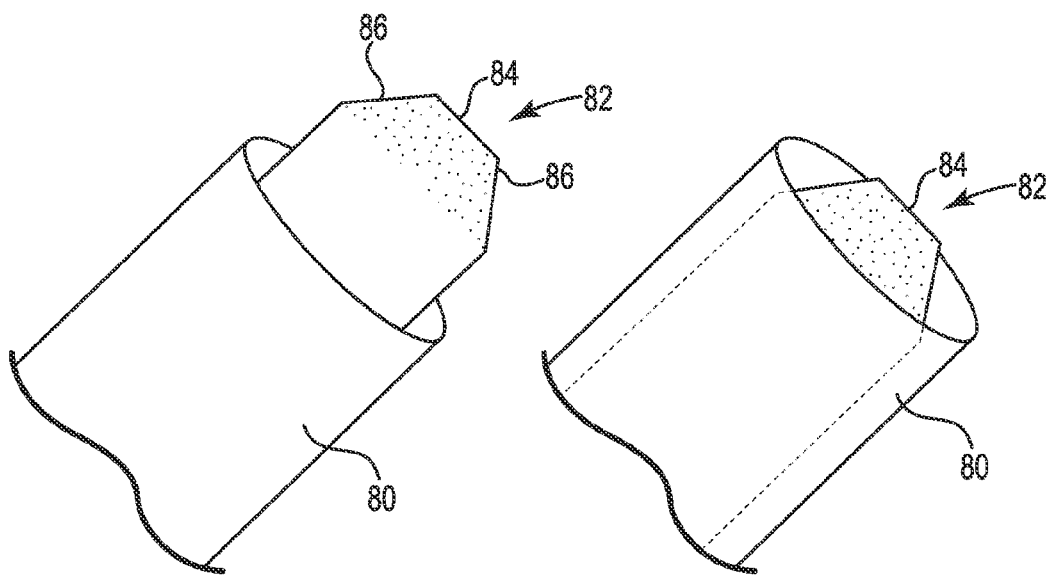
Fig. 8a    Fig. 8b

COMBINATION DIFFUSED AND FOCUSED FIBER OPTIC FOR DIAGNOSIS AND TREATMENT OF DISEASED CELLS

CROSS-REFERENCE TO RELATED APPLICATIONS

This application claims the benefit of U.S. Provisional Patent Application No. 61/777,187, filed Mar. 12, 2013 and titled "COMBINATION DIFFUSED AND FOCUSED FIBER OPTIC FOR DIAGNOSIS AND TREATMENT OF DISEASED CELLS" which application is incorporated herein by reference in its entirety.

TECHNICAL FIELD

Embodiments of the present invention relate generally to the diagnosis and treatment of diseased cells. More particularly, embodiments of the present invention relate to methods and devices for diagnosing and treating bladder cancer with a single instrument.

BACKGROUND

Bladder cancer can include a number of types of malignancy arising from the epithelial lining of the urinary bladder. A number of different symptoms can indicate the presence of bladder cancer, including blood in the urine, abdominal pain, urinary frequency, and painful urination, along with a number of other symptoms. If bladder cancer is suspected to be the cause of the patient's symptoms, additional steps to confirm the presence of cancer will typically be performed by a urologist or another physician that is trained in diagnosing bladder cancer.

A number of different medical procedures and tests can be used to diagnose the presence of bladder cancer in a patient, and to determine the precise location(s) of cancerous lesions and the severity of the cancer. Clinical trials have shown that photodynamic diagnosis (PDD) improves the ability to detect certain types of bladder cancer, which procedurally involves the use of fluorescence to locate abnormal tissue. PDD can be particularly effective in detecting cancers that include the presence of flat, urothelial, high-risk lesions. PDD involves instillation with a PDD agent such as hexylaminolevulinate, which can be referred to as "Hexvix" and which is commercially available under the trade name "Cysview". Hexvix induces the production of protoporphyrin IX (PpIX) in the bladder, wherein greater amounts of PpIX will build up in precancerous and cancerous lesions than in normal tissue, such that excitation of these lesions with blue light will produce different PpIX fluorescence than areas that do not include the precancerous or cancerous lesions. Thus, PDD requires a light source that provides such an excitation, along with specific lenses that enhance the contrast in fluorescence between benign and malignant tissue.

After a patient has been diagnosed with bladder cancer, either through the use of PDD or other diagnostic procedures, a treatment plan is typically developed, which may include surgical procedures, chemotherapy, and/or other approaches that are pursued at a later date from that of the diagnosis. Thus, there is a need to provide devices and methods that provide for accurate and timely diagnosis and treatment of bladder cancer in order to maximize the chances for the patient to achieve a full recovery.

SUMMARY

In order to visualize a bladder for cancer, in accordance with the present invention, photodynamic diagnosis (PDD), or auto fluorescence, can be used. As used with the devices and methods discussed herein, PDD includes the instillation of hexaminolevulinate into the bladder, which product can otherwise be referred to as Hexvix and/or by its trade name "Cysview". With this PDD process, blue light (e.g., blue light laser technology) will be used in order to diagnose areas of the bladder that include cancerous or precancerous lesions. Fiber optic technology can be used to deliver the blue light via a blue light laser system. Once cancerous or precancerous areas have been identified, treatment of the cancerous tissue can begin, and can be accomplished using the same device that is used for the diagnosis. This can be accomplished by the additional use of a blue light that is at higher power than was being used for diagnosis of the lesions. In accordance with the invention, the device and method include a lower power blue light that covers a relatively broad area for diagnosis and a higher power blue light that is more focused for accurate light delivery to only the tissue that is determined to be cancerous or precancerous, along with any desired surrounding margins.

In one embodiment, the present invention is directed to a method of treating diseased cells. The method comprises the steps of instilling an optical imaging agent to a tissue of a patient and accessing the tissue with a device comprising a fiber tip. The method also includes emitting a first light from the fiber tip and photodynamically diagnosing abnormal cells and emitting a second light from the fiber tip to treat the abnormal cells.

Another embodiment of the present invention is directed to a method of diagnosing and treating diseased cells. The method comprises the steps of delivering an optical imaging agent to a treatment region of a patient and delivering an optical device having a distal tip to the treatment region of the patient. In addition, the method includes emitting a first light from the optical device distal tip and photodynamically diagnosing abnormal cells in the treatment region. After the abnormal cells are identified, the abnormal cells are treated with a second power light.

A further embodiment of the present invention is directed to a method of diagnosing and treating abnormal tissue. The method comprises comprising the steps of delivering an optical imaging agent to a treatment region of a patient and delivering an optical fiber having a distal tip with at least one diffusion area and at least focused area to the treatment region of the patient. After the optical fiber is delivered to the treatment region, a first light is emitted from the at least one diffusion area of the optical fiber distal tip. The method also includes photodynamically diagnosing the abnormal tissue in the treatment region and vaporizing the abnormal tissue in the treatment region with a second light emitted through the at least one focused area of the optical fiber distal tip.

BRIEF DESCRIPTION OF THE DRAWINGS

The present invention will be further explained with reference to the appended Figures, wherein like structure is referred to by like numerals throughout the several views, and wherein:

FIGS. 7a and 7b are perspective views of an embodiment of a sleeve partially surrounding a fiber tip, with the sleeve in a retracted and advanced position relative to the tip, respectively; and FIGS. 8a and 8b are perspective views of another embodiment of a sleeve partially surrounding a fiber tip, with the sleeve in a retracted and advanced position relative to the tip, respectively.

DETAILED DESCRIPTION

Figure 1:
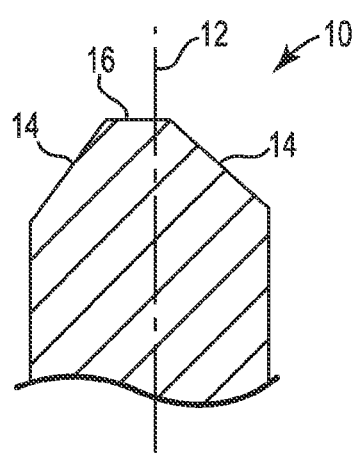
FIGS. 1-6 are cross-sectional side views of exemplary fiber tips that can be used with the devices and methods of the invention.

In accordance with embodiments of the present invention, a single device is used with photodynamic diagnosis (PDD), or auto fluorescence for both the diagnosis and treatment of bladder cancer. As used with the devices and methods discussed herein, PDD includes the instillation of hexaminolevulinate (Hexvix) into the bladder, or another optical imaging agent. In the use of this PDD process, fiber optic technology can be used to deliver blue light via blue light laser technology to diagnose areas of the bladder that include cancerous or precancerous lesions, and then treat these regions using a blue light that is at higher power than is being used for diagnosis of the lesions. In accordance with the invention, the device and method include a lower power blue light that covers a relatively broad area for diagnosis and a higher power blue light for vaporization that is more focused. The focusing of higher power blue light can provide for accurate vaporization of only targeted tissue that is determined to be cancerous or precancerous, along with any desired surrounding margins.

As is shown and described herein, one fiber of a fiber optic device can be used to transmit a diffused light/wavelength and also a more focused light/wavelength to certain bladder tissue. That is, a single fiber can be used for low power blue light PDD, and then subsequently used for precise, high power vaporization of target tissue or lesions. The use of a single device for both procedures eliminates the need to exchange devices between diagnosis or identification of target tissue or lesions and the treatment of these same areas, which provides for a process that can potentially save time and money while providing an improved treatment method.

One way of accomplishing this diagnosis and treatment with a single fiber is to provide a fiber with a polished surface that can be used for focused high-energy vaporization. This polished surface can be end firing, side firing, or a combination of end and side firing. In addition, at least one surface of this same fiber will include a diffusion or unpolished (e.g., rough) area that is separate from the polished area, which will be used for the lower energy PDD. The polished and unpolished areas can be on the same plane or separate planes or surfaces. With such a device, the same laser console can potentially create the low and high power light/signals, or separate laser consoles may be used, wherein the fiber is attached and detached from a low power laser console and a high power laser console, as needed or desired.

A sleeve or sheath may additionally or alternatively be used with a single fiber to help to block and/or direct the light. For example, an annular sleeve can be positioned for linear translation relative to a longitudinal axis of a fiber, for example, such that it can be advanced over at least a portion of the fiber tip, as needed or desired, to block the diffuse light and allow for the emission of a more focused light. The sleeve material that is positioned near the tip of the fiber is made of a material that can maintain its structural integrity during laser ablation. For example, the sleeve can be made of a material such as stainless steel or ceramic, and can be generally cylindrical or differently shaped at its distal end. The proximal end of the sleeve can have a number of different configurations that facilitate its retraction and advancement, such as telescopic or accordion-like, for example. Alternatively, the proximal end of the sleeve can be made of a material that is flexible enough that it can collapse on itself during the linear retraction and advancement of the sleeve relative to the distal end of the fiber.

Referring now to the Figures, wherein the components are labeled with like numerals throughout the several Figures, and initially to FIG. 1, an exemplary cross-sectional view of a distal end or tip 10 of a fiber is shown, which is asymmetric about a longitudinal axis 12. The tip 10 includes diffusion areas 14 and a focused area 16, wherein the diffusion areas 14 can provide lower energy blue light emission for PDD and the focused area 16 can provide higher energy blue light emission for vaporization or ablation of tissue. Such a tip can be considered to be end-firing in that the higher energy blue light will exit from the distal end of the tip 10.

Figure 2:
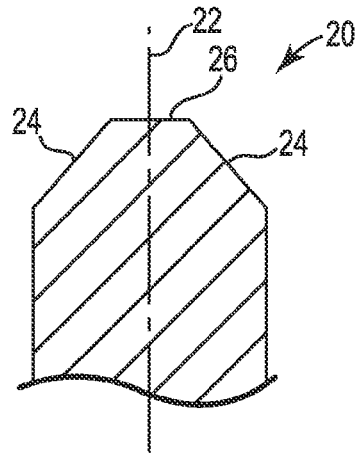

FIG. 2 illustrates another distal end or tip 20 of a fiber, which is similar to the tip 10 of FIG. 1, but instead is symmetric about a longitudinal axis 22. The tip 20 also includes diffusion areas 24 and a focused area 26, wherein the diffusion areas 24 can provide lower energy blue light emission for PDD and the focused area 26 can provide higher energy blue light emission for vaporization or ablation of tissue. Such a tip can be considered to be end-firing in that the higher energy blue light will exit from the distal end of the tip 20.

Figure 3:
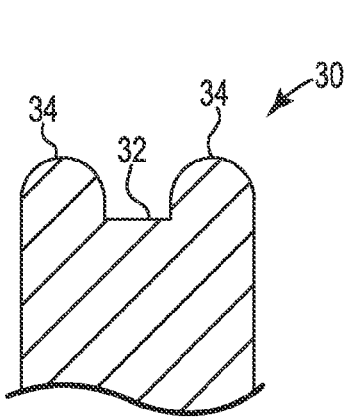

FIG. 3 illustrates another distal end or tip 30 of a fiber, which includes a central depressed area 32 that is surrounded or partially surrounded by raised areas 34. The depressed area 32 can be considered to be the area that provides for higher energy blue light emission for vaporization or ablation of tissue, while the raised areas 34 can be considered to be diffusion areas that can provide lower energy blue light emission for PDD. Such a tip can be considered to be end-firing in that the higher energy blue light will exit from the distal end of the tip 30.

Figure 4:
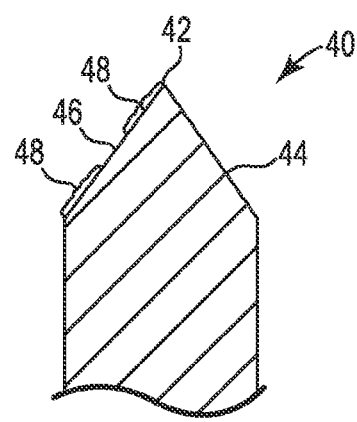

FIG. 4 illustrates another distal end or tip 40 of a fiber, which includes a pointed tip 42 with a first diffusion area 44 on one side of the tip 42 and at least one focused area 46 between one or more diffusion zones 48 on the opposite side of the tip 42. The configuration of the diffusion zones 48 relative to the focused area 46 can include a wide variety of sizes and shapes. For one example, the focused area 46 can be circular in shape and surrounded by a single diffusion zone 48. For another example, the focused area 46 can be a square or stripe that is surrounded by one or more diffusion zones 48. In any case, the focused area 46 can be considered to be the area that provides for higher energy blue light emission for vaporization or ablation of tissue, while the first diffusion area 44 and the diffusion zone(s) 48 can be considered to be diffusion areas that can provide lower energy blue light emission for PDD. Such a tip can be considered to be side-firing in that the higher energy blue light will exit from a side area of the tip 40.

Figure 5:
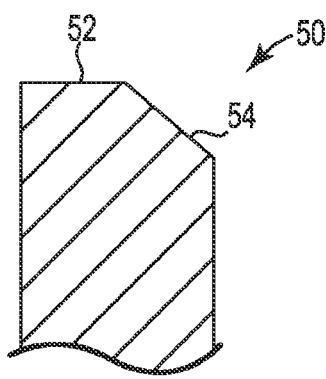

FIG. 5 illustrates another distal end or tip 50 of a fiber, which includes a flat surface 52 from which an angled surface 54 extends. Either or both of these surfaces 52, 54 can include one or more portions that are considered to be focused or higher energy area(s), along with one or more portions that are considered to be diffusion or lower energy area(s). The configuration of the diffusion zone(s) relative to the focused zone(s) can include a wide variety of sizes and shapes. It is contemplated that one of the surfaces 52, 54 can be entirely a higher energy or focused surface, while the other of the surfaces 52, 54 can be entirely a lower energy or diffusion surface. Such a tip 50 can be considered to be either end-firing or side-firing, depending on which area of the tip 50 includes the higher energy or focused area(s).

Figure 6:
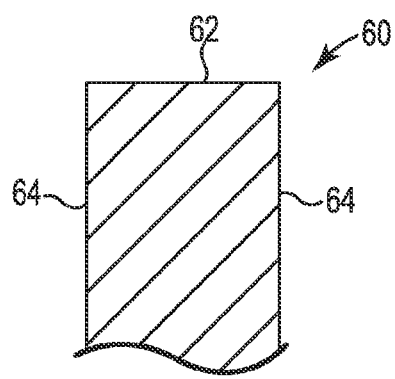

FIG. 6 illustrates another distal end or tip 60 of a fiber, which includes a single surface 62 that is shown as being generally planar and perpendicular to the sides 64 of the tip 60, although it is understood that the surface 62 can be at least slightly angled relative to the sides 64. The surface 62 can include a combination of higher energy or focused surface(s) and lower energy or diffused surface(s). Such a tip can be considered to be end-firing in that the higher energy blue light will exit from the distal end of the tip 60. With this and the other illustrated embodiments, the higher energy area(s) can generally have a smoother surface than the relatively rough surface of the lower energy area(s).

FIGS. 7a and 7b are perspective views of an embodiment of a sleeve 70 partially surrounding a fiber tip 72, with the sleeve 70 in a retracted and advanced position relative to the tip, respectively. In this embodiment, the tip 72 is illustrated as having a curved tip surface that allows for diffuse or lower energy light emission when it is advanced or extended relative to the sleeve 70, and wherein this light emission will be more focused or directed when the tip 72 is retracted relative to the sleeve 70. That is, because more of the tip 72 is covered when it is surrounded by the sleeve 70, the emitted light will all be directed from the opening at the end of the sleeve 70. As is discussed above, the sleeve 70 can be advanced and retracted as needed or desired to block diffuse light and allow for the emission of a more focused light. The material from which the sleeve is made in the area adjacent to the tip of the fiber is a material that can maintain its structural integrity during the emission of higher energy light or laser ablation.

FIGS. 8a and 8b are perspective views of an embodiment of a sleeve 80 partially surrounding a fiber tip 82, with the sleeve 80 in a retracted and advanced position relative to the tip, respectively. In this embodiment, the tip 82 is illustrated as having a flat surface 84 and angled surfaces 86, similar to the tips illustrated in FIGS. 1 and 2. That is, the flat surface 84 functions as a focused area and the angled surfaces 86 function as diffusion areas, wherein the diffusion areas can provide lower energy blue light emission for PDD and the focused area can provide higher energy blue light emission for vaporization or ablation of tissue. Such a tip can be considered to be end-firing in that the higher energy blue light will exit from the distal end of the tip 82. With this embodiment, the use of the sleeve 80 further allows for diffuse or lower energy light emission when the tip 82 is advanced or extended relative to the sleeve 80, and wherein this light emission will be more focused or directed when the tip 82 is retracted relative to the sleeve 80. That is, because more of the tip 82 is covered when it is surrounded by the sleeve 80, the emitted light will be directed from the opening at the end of the sleeve 80. As is discussed above, the sleeve 80 can be advanced and retracted as needed or desired to block diffuse light and allow for the emission of a more focused light. The material from which the sleeve is made in the area adjacent to the tip of the fiber is made of a material that can maintain its structural integrity during the emission of higher energy light or laser ablation.

While the description provided herein is directed to the diagnosis and treatment of bladder cancer, the methods and devices described herein can also be used for other the diagnosis and treatment of other types of diseased cells that can be visualized and treated using light of different power levels, such as cells or tissue for which photodynamic diagnosis is effective. Further, the various fiber tips shown and described herein are intended to be exemplary, and it is contemplated that a wide variety of shapes and surfaces can be used for the fiber tips, including surfaces that are angled, flat, curved, curvilinear, and the like. It is further contemplated that the system includes software that can be used so that a focused section of the fiber optic can send a diagnostic signal to the tissue, read the tissue signature, and then use the focused or diffused light to treat the tissue. In this scenario, the instilling of an optical imaging agent may be optional. In addition, the use of a combined focused and diffused fiber can include using the focused area treat the abnormal cells, and the diffused area to help coagulate, seal, or promote healing for the surrounding tissues for less bleeding and improved healing during the procedure. In this case, the treatment light could emit from the focused and diffused areas at the same time or at different times.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention.

The invention claimed is:

1. A method of treatment, the method comprising the steps of:
   delivering an optical imaging agent to a tissue;
   accessing the tissue with a device comprising a sleeve with a lumen, an optical fiber in the lumen, and a fiber tip on the optical fiber;
   moving the optical fiber relative to the lumen until a diffused area of the fiber tip is out of the lumen;
   emitting a first light from a light source through the optical fiber and the at least one diffused area of the fiber tip to photodynamically identify a treatment area on the tissue;
   moving the optical fiber relative to the lumen until at least a portion of the diffused area is in the lumen; and
   emitting a second light from the light source through the optical fiber and a focused area of the fiber tip to treat the treatment area.

2. The method of claim 1, wherein the first light is a first power blue light and the second light is a second power blue light.

3. The method of claim 2, wherein the first power blue light is a lower power than the second power blue light.

4. The method of claim 1, wherein the optical imaging agent comprises hexylaminolevulinate.

5. The method of claim 1, wherein the treatment area comprises a bladder tissue.

6. The method of claim 5, wherein the treatment area comprises at least one of cancerous cells and precancerous cells.

7. The method of claim 1, wherein the least one focused area includes a depressed surface of the fiber tip and the at least one diffused area includes raised surface that surrounds the depressed surface.

8. The method of claim 7, wherein the depressed surface is an end firing surface of the fiber tip and a portion of the raised surface is a side firing surface of the fiber tip.

9. A method of treatment, the method comprising the steps of:
   delivering an optical imaging agent to a treatment region;
   delivering a sleeve with a lumen to the treatment region;
   delivering a distal tip of an optical fiber to the treatment region through the lumen;
   moving a diffused area on the distal tip out of the lumen;

emitting a first light from the light source through the optical fiber and the diffused area of the distal tip;

photodynamically identifying a treatment area in the treatment region with the first light;

moving the diffused area into the lumen;

emitting a second light from the light source through the optical fiber and a focused area of the distal tip; and treating the treatment area with the second light.

10. The method of claim 9, wherein the first light has a first power and the second light has a second power.

11. The method of claim 10, wherein the first power is lower than the second power.

12. The method of claim 9, wherein the first light and the second light are blue light.

13. The method of claim 9, wherein the optical imaging agent comprises hexylaminolevulinate.

14. The method of claim 9, wherein the treatment region is a bladder and the treatment area comprises a bladder tissue.

15. The method of claim 9, wherein the treatment area comprises at least one of cancerous cells and precancerous cells.

16. The method of claim 9, wherein the focused area is a polished end firing surface of the distal tip and the diffused area is an unpolished side firing surface of the distal tip.

17. The method of claim 9, wherein treating the treatment area comprises vaporizing a portion of the treatment area.

18. A method of treatment, the method comprising the steps of:

delivering an optical imaging agent to a treatment region;

delivering a sleeve with a lumen to the treatment region;

delivering a distal tip of an optical fiber to the treatment region through the lumen, the distal tip including a side firing surface and an end firing surface;

moving the optical fiber out of the lumen until the side firing surface is adjacent the treatment region;

emitting a first light from the light source through the optical fiber and at least one diffused area on the side firing surface;

photodynamically identifying a treatment area in the treatment region with the first light;

moving the optical fiber into the lumen until the end firing surface is aligned with the treatment area;

emitting a second light from the light source through the single optical fiber and at least one focused area on the end firing surface; and vaporizing a portion of the treatment area with the second light.

19. The method of claim 1, further comprising the steps of:

delivering a diagnostic signal from the optical fiber to the treatment area; and reading a tissue signature from the diagnostic signal.

20. The method of claim 19, further comprising the steps of:

delivering a diagnostic signal from the optical fiber to the treatment area; and reading a tissue signature from the diagnostic signal.

* * * * *